United States Patent
Richard (10) Patent No.: US 11,696,764 B2
(45) Date of Patent: Jul. 11, 2023

(54) LIGATION CLIP WITH CONTROLLED TISSUE COMPRESSION

(71) Applicant: Covidien LP, Mansfield, MA (US)

(72) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 317 days.

(21) Appl. No.: 17/096,330

(22) Filed: Nov. 12, 2020

(65) Prior Publication Data

US 2021/0236133 A1 Aug. 5, 2021

Related U.S. Application Data

(60) Provisional application No. 62/968,385, filed on Jan. 31, 2020.

(51) Int. Cl.
*A61B 17/122* (2006.01)
*A61B 17/00* (2006.01)

(52) U.S. Cl.
CPC ............ *A61B 17/1227* (2013.01); *A61B 2017/00477* (2013.01); *A61B 2017/00526* (2013.01); *A61B 2017/00862* (2013.01)

(58) Field of Classification Search
CPC . A61B 17/083; A61B 17/122; A61B 17/1227; A61F 6/206
See application file for complete search history.

(56) References Cited

U.S. PATENT DOCUMENTS

| | | | |
|---|---|---|---|
| 3,040,749 A | 6/1962 | Payton | |
| 3,439,523 A | 4/1969 | Wood | |
| 3,629,912 A * | 12/1971 | Klopp | G03D 13/10 24/535 |
| 3,713,533 A | 1/1973 | Reimels | |
| 3,766,925 A * | 10/1973 | Rubricius | A61B 17/122 606/120 |
| 3,926,175 A * | 12/1975 | Allen | A61F 2/0036 251/9 |
| 4,076,120 A | 2/1978 | Carroll et al. | |
| 4,146,130 A | 3/1979 | Samuels et al. | |
| 4,187,712 A | 2/1980 | Samuels et al. | |
| 4,212,303 A | 7/1980 | Nolan | |
| 4,212,390 A | 7/1980 | Raczkowski et al. | |
| 4,294,355 A | 10/1981 | Jewusiak et al. | |
| 4,344,531 A | 8/1982 | Giersch | |
| 4,346,869 A | 8/1982 | MacNeill | |

(Continued)

FOREIGN PATENT DOCUMENTS

| | | |
|---|---|---|
| BE | 654195 A | 2/1965 |
| CN | 204839635 U | 12/2015 |

(Continued)

OTHER PUBLICATIONS

Chinese International PCT Application No. PCT/CN2018/078294 filed Mar. 7, 2018, Covidien LP.

*Primary Examiner* — Ryan J. Severson
(74) *Attorney, Agent, or Firm* — Carter, DeLuca & Farrell LLP (57) ABSTRACT

A ligation clip includes a frame defining a cavity, a flexible band that is pivotably supported on one end of the frame, and a spring beam supported on the other end of the frame in cantilevered fashion. The flexible band is movable in relation to the frame from an open position to a clamped position to clamp tissue between the flexible band and the spring beam.

20 Claims, 5 Drawing Sheets

(56) References Cited

U.S. PATENT DOCUMENTS

| | | | |
|---|---|---|---|
| 4,361,229 A | 11/1982 | Mericle | |
| 4,390,019 A | 6/1983 | LeVeen et al. | |
| 4,412,617 A | 11/1983 | Cerwin | |
| 4,418,694 A | 12/1983 | Beroff et al. | |
| 4,449,531 A | 5/1984 | Cerwin et al. | |
| 4,458,682 A * | 7/1984 | Cerwin | A61B 17/122 606/158 |
| 4,476,865 A | 10/1984 | Failla et al. | |
| 4,478,218 A | 10/1984 | Mericle | |
| 4,485,953 A | 12/1984 | Rothfuss | |
| 4,487,205 A | 12/1984 | Di Giovanni et al. | |
| 4,550,729 A | 11/1985 | Cerwin et al. | |
| 4,696,396 A | 9/1987 | Samuels | |
| 4,726,372 A | 2/1988 | Perlin | |
| 4,822,348 A * | 4/1989 | Casey | A61F 6/206 606/157 |
| 4,834,096 A | 5/1989 | Oh et al. | |
| 4,936,447 A | 6/1990 | Peiffer | |
| 4,942,886 A | 7/1990 | Timmons | |
| 4,961,499 A | 10/1990 | Kulp | |
| 4,971,198 A | 11/1990 | Mericle | |
| 4,972,949 A | 11/1990 | Peiffer | |
| 5,002,552 A * | 3/1991 | Casey | A61F 6/206 606/135 |
| 5,046,611 A | 9/1991 | Oh | |
| 5,046,624 A | 9/1991 | Murphy et al. | |
| 5,050,272 A | 9/1991 | Robinson et al. | |
| 5,062,846 A | 11/1991 | Oh et al. | |
| 5,078,731 A * | 1/1992 | Hayhurst | A61B 17/1285 606/232 |
| 5,100,416 A | 3/1992 | Oh et al. | |
| 5,201,416 A | 4/1993 | Taylor | |
| 5,222,961 A | 6/1993 | Nakao et al. | |
| 5,234,449 A | 8/1993 | Bruker et al. | |
| 5,279,416 A | 1/1994 | Malec et al. | |
| 5,423,831 A | 6/1995 | Nates | |
| 5,462,555 A | 10/1995 | Bolanos et al. | |
| 5,474,572 A * | 12/1995 | Hayhurst | A61B 17/122 606/232 |
| 5,564,262 A | 10/1996 | Bevis et al. | |
| 5,575,802 A | 11/1996 | McQuilkin et al. | |
| 5,634,930 A | 6/1997 | Thornton et al. | |
| 5,676,676 A | 10/1997 | Porter | |
| 5,695,505 A * | 12/1997 | Yoon | A61B 17/12 606/151 |
| 5,697,942 A | 12/1997 | Palti | |
| 5,713,912 A | 2/1998 | Porter | |
| 5,846,255 A | 12/1998 | Casey | |
| 5,908,430 A | 6/1999 | Appleby | |
| 5,921,991 A | 7/1999 | Whitehead et al. | |
| D417,837 S * | 12/1999 | Nakamura | D9/434 |
| 6,044,971 A | 4/2000 | Esposito et al. | |
| 6,158,583 A | 12/2000 | Forster | |
| 6,210,419 B1 * | 4/2001 | Mayenberger | A61B 17/122 606/151 |
| 6,217,590 B1 | 4/2001 | Levinson | |
| 6,228,097 B1 | 5/2001 | Levinson et al. | |
| 6,273,253 B1 | 8/2001 | Forster et al. | |
| D447,564 S * | 9/2001 | Stewart, Jr. | D8/395 |
| 6,306,150 B1 | 10/2001 | Levinson | |
| 6,349,727 B1 | 2/2002 | Stewart, Jr. | |
| 6,391,035 B1 | 5/2002 | Appleby et al. | |
| 6,419,682 B1 | 7/2002 | Appleby et al. | |
| 6,421,920 B1 | 7/2002 | Jensen | |
| 6,439,727 B1 | 8/2002 | Koide | |
| 6,460,700 B2 | 10/2002 | Weisshaupt | |
| 6,460,749 B1 | 10/2002 | Levinson et al. | |
| 6,699,258 B1 * | 3/2004 | Sadler | A61B 17/122 606/157 |
| 6,780,195 B2 | 8/2004 | Porat | |
| 6,824,547 B2 | 11/2004 | Wilson, Jr. et al. | |
| 6,863,675 B2 | 3/2005 | Wilson, Jr. | |
| 6,880,699 B2 | 4/2005 | Gallagher | |
| 7,001,412 B2 | 2/2006 | Gallagher et al. | |
| 7,052,504 B2 | 5/2006 | Hughett | |
| 7,131,977 B2 | 11/2006 | Fowler | |
| 7,144,402 B2 | 12/2006 | Kuester, III | |
| 7,181,806 B2 * | 2/2007 | Folkmar | B65D 33/1675 24/30.5 R |
| 7,211,091 B2 | 5/2007 | Fowler et al. | |
| 7,211,092 B2 | 5/2007 | Hughett | |
| 7,316,696 B2 | 1/2008 | Wilson, Jr. et al. | |
| 7,326,223 B2 | 2/2008 | Wilson, Jr. | |
| 7,452,368 B2 | 11/2008 | Liberatore et al. | |
| 7,585,304 B2 | 9/2009 | Hughett | |
| 7,628,272 B2 | 12/2009 | Wiedenbein | |
| 7,857,129 B2 | 12/2010 | Iaconi-Forrer et al. | |
| 8,042,687 B2 | 10/2011 | Cannady | |
| 8,100,926 B1 * | 1/2012 | Filshie | A61B 17/122 606/151 |
| 8,312,992 B2 | 11/2012 | Disch | |
| 8,403,138 B2 | 3/2013 | Weisshaupt et al. | |
| 8,425,515 B2 | 4/2013 | Gamache et al. | |
| 8,627,955 B2 | 1/2014 | Weisshaupt et al. | |
| 8,839,954 B2 | 9/2014 | Disch | |
| 8,888,398 B2 | 11/2014 | Werth | |
| 9,271,737 B2 | 3/2016 | Castro et al. | |
| 9,282,972 B1 | 3/2016 | Patel et al. | |
| 9,445,820 B2 | 9/2016 | Whiting | |
| 9,456,824 B2 | 10/2016 | Willett et al. | |
| 9,480,480 B2 | 11/2016 | Santilli et al. | |
| 9,486,225 B2 | 11/2016 | Michler et al. | |
| 9,517,178 B2 | 12/2016 | Chancibot | |
| D808,522 S | 1/2018 | Cannady et al. | |
| 9,855,053 B2 | 1/2018 | Bagaoisan et al. | |
| 9,901,352 B2 * | 2/2018 | Fago | A61B 17/1227 |
| 10,064,623 B2 * | 9/2018 | Soutorine | A61B 17/122 |
| 10,130,373 B2 | 11/2018 | Castro et al. | |
| 10,136,898 B2 | 11/2018 | Schmidt et al. | |
| 10,136,899 B2 * | 11/2018 | Jensen | A61B 17/128 |
| 10,258,345 B2 * | 4/2019 | Brown | A61B 17/122 |
| 10,542,998 B2 * | 1/2020 | Whiting | A61B 17/122 |
| 10,548,609 B2 * | 2/2020 | Ramsey | A61B 17/122 |
| 10,687,822 B2 * | 6/2020 | Bachar | A61B 17/122 |
| 2002/0046961 A1 | 4/2002 | Levinson et al. | |
| 2002/0177863 A1 | 11/2002 | Mandel et al. | |
| 2004/0199178 A1 | 10/2004 | Small | |
| 2005/0149069 A1 * | 7/2005 | Bertolero | A61B 1/12 606/151 |
| 2005/0165423 A1 | 7/2005 | Gallagher et al. | |
| 2005/0165424 A1 | 7/2005 | Gallagher et al. | |
| 2006/0089659 A1 | 4/2006 | Small | |
| 2006/0124485 A1 | 6/2006 | Kennedy | |
| 2006/0217749 A1 | 9/2006 | Wilson et al. | |
| 2007/0083218 A1 | 4/2007 | Morris | |
| 2007/0118161 A1 | 5/2007 | Kennedy et al. | |
| 2007/0149988 A1 | 6/2007 | Michler et al. | |
| 2007/0149989 A1 | 6/2007 | Santilli et al. | |
| 2008/0039879 A1 * | 2/2008 | Chin | A61B 17/064 606/157 |
| 2009/0088783 A1 | 4/2009 | Kennedy et al. | |
| 2009/0171380 A1 | 7/2009 | Whiting | |
| 2011/0224700 A1 | 9/2011 | Schmidt et al. | |
| 2011/0295291 A1 | 12/2011 | Trivisani | |
| 2012/0083803 A1 | 4/2012 | Patel et al. | |
| 2012/0226291 A1 | 9/2012 | Malizia et al. | |
| 2013/0245651 A1 | 9/2013 | Schmidt et al. | |
| 2013/0253540 A1 | 9/2013 | Castro et al. | |
| 2013/0261642 A1 | 10/2013 | Willett et al. | |
| 2014/0025092 A1 | 1/2014 | Ewers et al. | |
| 2014/0054192 A1 | 2/2014 | Chancibot | |
| 2014/0058411 A1 * | 2/2014 | Soutorine | A61B 17/128 606/151 |
| 2014/0236170 A1 | 8/2014 | Kethman et al. | |
| 2014/0243862 A1 | 8/2014 | Bagaoisan et al. | |
| 2014/0276970 A1 | 9/2014 | Messerly et al. | |
| 2016/0151073 A1 | 6/2016 | Castro et al. | |
| 2016/0354089 A1 | 12/2016 | Whiting | |
| 2017/0020530 A1 | 1/2017 | Willett et al. | |
| 2017/0027576 A1 | 2/2017 | Castro | |
| 2017/0209151 A1 | 7/2017 | Brown | |
| 2017/0238935 A1 | 8/2017 | Shi | |
| 2017/0252042 A1 | 9/2017 | Kethman et al. | |

(56) References Cited

U.S. PATENT DOCUMENTS

| | | | |
|---|---|---|---|
| 2018/0036008 A1 | 2/2018 | Ramsey et al. | |
| 2018/0146965 A1* | 5/2018 | Bachar | A61B 17/122 |
| 2018/0168659 A1 | 6/2018 | Bagaoisan et al. | |
| 2018/0185029 A1 | 7/2018 | Lebens, III | |
| 2018/0228492 A1 | 8/2018 | Aranyi et al. | |
| 2018/0263628 A1* | 9/2018 | Bachar | A61B 17/1285 |
| 2018/0271527 A1 | 9/2018 | Shellenberger | |
| 2018/0271532 A1 | 9/2018 | Shellenberger | |
| 2018/0271535 A1 | 9/2018 | Shellenberger et al. | |
| 2018/0271536 A1 | 9/2018 | Shellenberger et al. | |
| 2019/0133590 A1 | 5/2019 | Richard | |
| 2019/0159782 A1 | 5/2019 | Kamaraj et al. | |
| 2019/0223874 A1 | 7/2019 | Pilletere et al. | |
| 2020/0360021 A1* | 11/2020 | Foshee | A61B 17/122 |
| 2021/0236133 A1* | 8/2021 | Richard | A61B 17/1227 |

FOREIGN PATENT DOCUMENTS

| | | |
|---|---|---|
| CN | 106264647 A | 1/2017 |
| DE | 10116168 A1 | 11/2001 |
| EP | 3046482 A1 | 7/2016 |
| EP | 3305217 A1 | 4/2018 |
| EP | 3400887 A1 | 11/2018 |
| GB | 2353710 A | 3/2001 |

\* cited by examiner

LIGATION CLIP WITH CONTROLLED TISSUE COMPRESSION

CROSS-REFERENCE TO RELATED APPLICATION

The present application claims the benefit of and priority to U.S. Provisional Patent Application Ser. No. 62/968,385, filed on Jan. 31, 2020, the entire content of which is incorporated by reference.

FIELD

This disclosure is generally related to ligation clips and, more particularly, to ligation clips that are adjustable to accommodate tissues of variable thickness.

BACKGROUND

Polymeric ligation clips typically include first and second beams that are coupled together at one end by a pivotable connection, e.g., living hinge, such that the first and second beams can be moved in relation to each other between open and clamped positions. The ligation clips can be applied to tissue endoscopically through a small diameter incision or through a small diameter cannula positioned through the incision to minimize trauma to a patient during a surgical procedure.

A continuing need exists for a ligation clip that is simple in design, is inexpensive to manufacture, has a low profile for improved visualization at a surgical site, and is capable of controlled tissue compression.

SUMMARY

Aspects of the disclosure are directed to a ligation clip that includes a frame defining a cavity, a flexible band that is pivotably supported on one end of the frame, and a spring beam supported on the other end of the frame in cantilevered fashion. The flexible band is movable in relation to the frame from an open position to a clamped position to clamp tissue between the flexible band and the spring beam. The spring beam in association with the frame and flexible band provides controlled tissue compression to minimize ischemic tissue damage.

In one aspect of the disclosure, a ligation clip includes a frame, a flexible band, and a spring beam. The frame has a first end portion, a second end portion, and spaced side walls. The frame defines a cavity between the side walls. The second end portion of the frame defines a latch receiver. The flexible band has a first end portion coupled to the first end portion of the frame and a second end portion supporting a latch. The flexible band is movable in relation to the frame from an open position to a clamped position. The latch is received within the latch receiver in the clamped position to retain the flexible band in the clamped position. The spring beam is secured to the second end portion of the frame in cantilevered fashion and is extends over the cavity defined by the frame.

Other aspects of the disclosure are directed to a ligation clip including a frame, a flexible band, and a spring beam. The frame has a first end portion, a second end portion, and spaced side walls to form a rectangular configuration defining a cavity between the side walls. The second end portion of the frame defines a latch receiver. The flexible band has a first end portion coupled to the first end portion of the frame and a second end portion supporting a latch. The flexible band is movable in relation to the frame from an open position to a clamped position. The latch is received within the latch receiver in the clamped position to retain the flexible band in the clamped position. The spring beam is secured in cantilevered fashion to the second end portion of the frame and is positioned over the cavity defined by the frame. The spring beam includes a curved body having a central portion that bows upwardly away from the cavity of the frame.

Yet other aspects of the disclosure are directed to a ligation clip including a frame, a flexible band, and a spring beam. The frame has a first end portion, a second end portion, and spaced side walls that form a rectangular configuration. The frame defines a cavity between the side walls. The second end portion of the frame defines a latch receiver that includes a latch slot that defines a shoulder. The flexible band has a first end portion that is coupled to the first end portion of the frame and a second end portion that supports a latch. The flexible band is movable in relation to the frame from an open position to a clamped position. The latch includes a flexible tab that is received within the latch slot of the latch receiver. The flexible tab of the latch supports a detent that engages the shoulder defined within the latch slot when the flexible beam is in the clamped position to retain the flexible beam in the clamped position. The spring beam is secured in cantilevered fashion to the second end portion of the frame and is positioned over the cavity defined by the frame.

In aspects of the disclosure, the frame has a rectangular configuration.

In some aspects of the disclosure, the flexible band is coupled to the first end portion of the frame by a living hinge.

In certain aspects of the disclosure, the flexible beam is coupled to the frame by a pivot pin.

In aspects of the disclosure, the first end portion of the frame includes a first hinge portion and the first end portion of the flexible band includes second hinge portion that is coupled to the first hinge portion by the pivot pin.

In aspects of the disclosure, the first end portion of the frame is coupled to the first end portion of the flexible band by a dove-tail type connection.

In some aspects of the disclosure, the latch receiver includes a latch slot that receives the latch to retain the flexible beam in the clamped position.

In certain aspects of the disclosure, the latch slot defines a shoulder.

In aspects of the disclosure, the latch includes a flexible tab that is received within the latch slot when the flexible beam is in the clamped position.

In some aspects of the disclosure, the flexible tab of the latch supports a detent that engages the shoulder defined within the latch slot when the flexible beam is in the clamped position to retain the flexible beam in the clamped position.

In certain aspects of the disclosure, the ligation clip is formed as a single piece using a molding process.

In aspects of the disclosure, the spring beam includes a curved body that is formed of a resilient material and includes a central portion that bows upwardly away from the cavity of the frame.

In some aspects of the disclosure, the latch slot includes an inlet opening that defines an inwardly tapered guide surface.

Other features of the disclosure will be appreciated from the following description.

BRIEF DESCRIPTION OF THE DRAWINGS

Various aspects of the disclosed two piece ligation clips are described herein below with reference to the drawings, wherein.

DETAILED DESCRIPTION

The disclosed ligation clip will now be described in detail with reference to the drawings in which like reference numerals designate identical or corresponding elements in each of the several views. However, it is to be understood that the disclosed aspects of the ligation clip are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as upper, lower, top, bottom, and similar terms are used to assist in understanding the description and are not intended to limit the disclosure.

In this description, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel. Finally, the term "substantially" is used generally to refer to 90 percent to 110 percent of a referenced parameter.

The disclosed ligation clip includes a frame having a first end and a second end, a flexible band that is hinged to the first end of the frame, and a spring beam that is secured in a cantilevered fashion to the second end of the frame. The flexible band includes a zip-tie like latch and the frame includes a latch receiver on its second end. The flexible band can be stretched over the frame and latched to the latch receiver on the frame to compress tissue positioned between the flexile band and the spring beam. The spring beam applies a controlled pressure to tissue clamped between the flexible band and the spring beam to minimize ischemic tissue damage. The configuration of the ligation clip is low profile to improve visualization at a surgical site and allows for manufacture with non-engineering grade materials.

Figure 1:
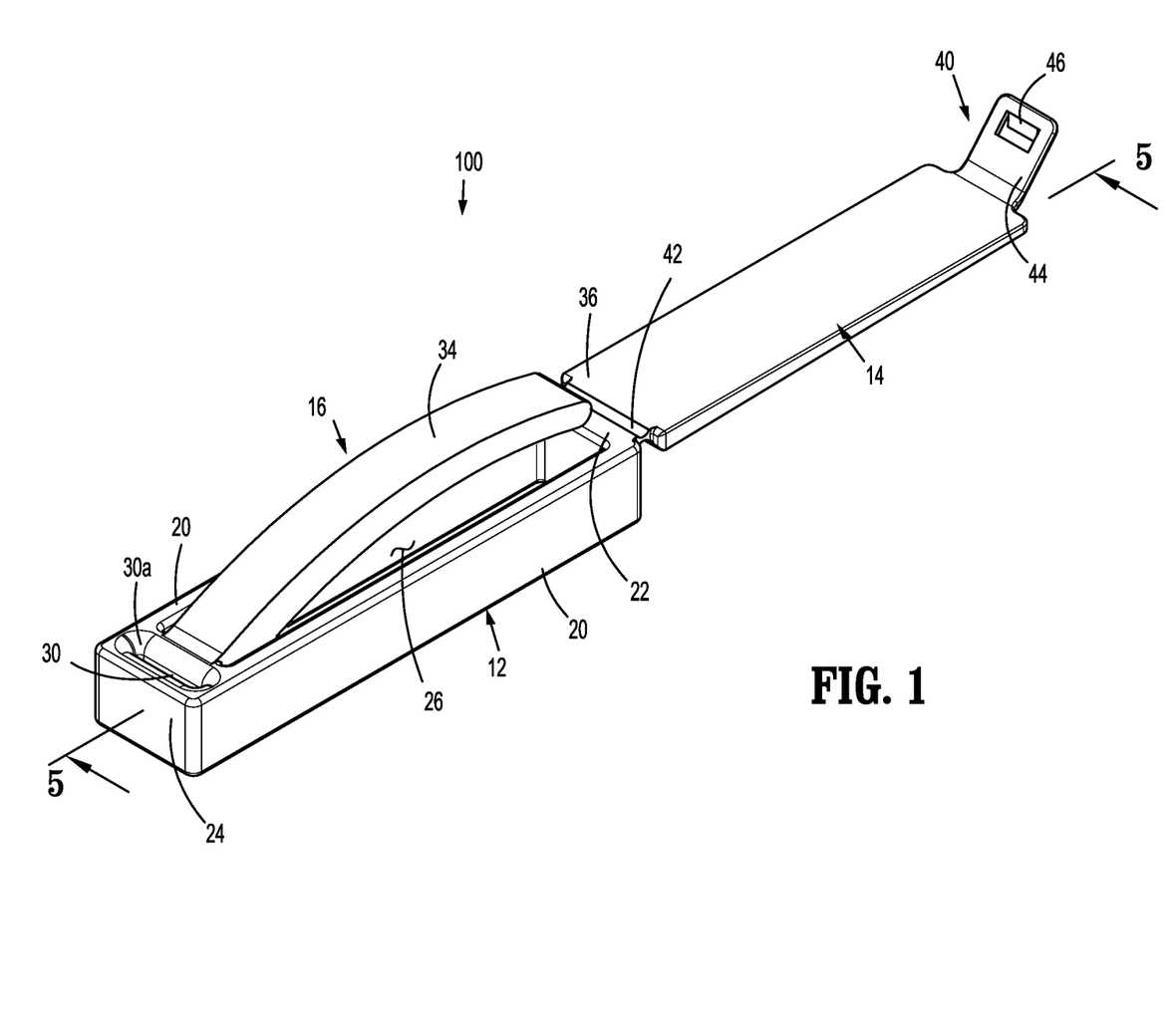
FIG. 1 is a side perspective view of a ligation clip in an open position including aspects of the disclosure.
Figure 2:
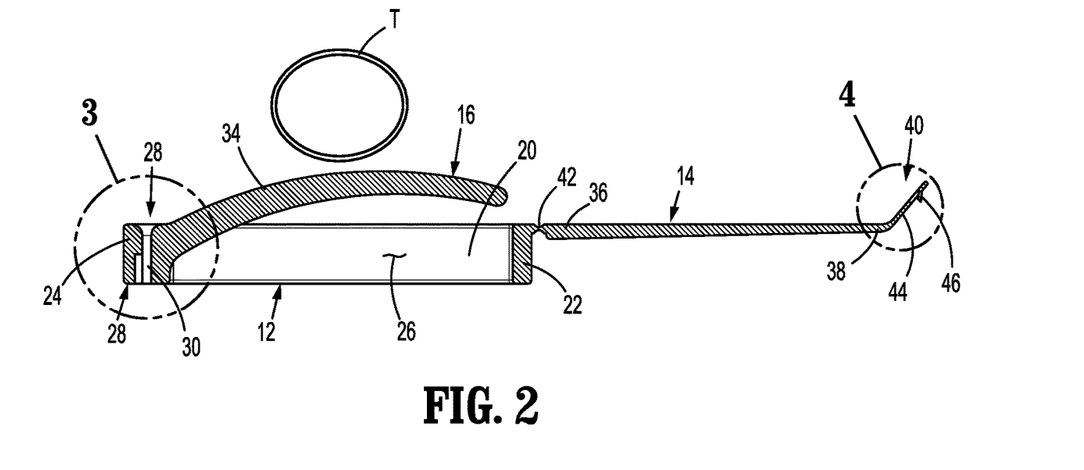
FIG. 2 is a cross-sectional view taken along section lines 5-5 of FIG. 1.
Figures 3, 4:
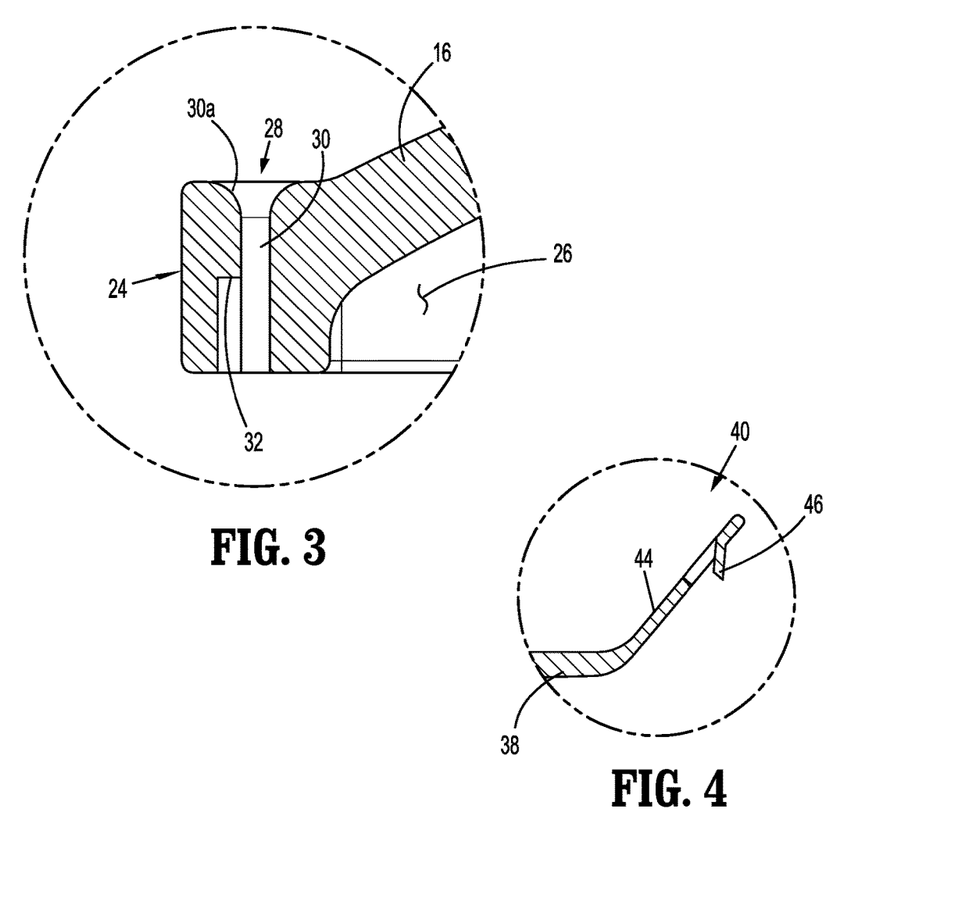
FIG. 3 is an enlarged view of the indicated area of detail shown in FIG. 2.
FIG. 4 is an enlarged view of the indicated area of detail shown in FIG. 2

The disclosed ligation clip is shown generally in FIGS. 1-6 as ligation clip 10. FIGS. 1-4 illustrate the ligation clip 10 in an open position. The ligation clip 10 includes a frame 12, a flexible band 14, and a spring beam 16. In aspects of the disclosure, the frame 12 has a rectangular configuration and includes side walls 20, a first end wall 22, and a second end wall 24 that together define a cavity 26. The second end wall 24 of the frame 12 includes a latch receiver 28 which includes a stepped latch slot 30 that defines a shoulder 32. The entrance or inlet to the latch slot 30 may include an inwardly tapered guide surface 30a (FIG. 3).

The spring beam 16 is secured to the second end wall 24 of the frame 12 and extends in cantilevered fashion over the cavity 26. In aspects of the disclosure, the spring beam 16 includes a curved body 34 that is formed of a resilient material and includes a central portion that bows upwardly away from the cavity 26 of the frame 12.

Figure 7:
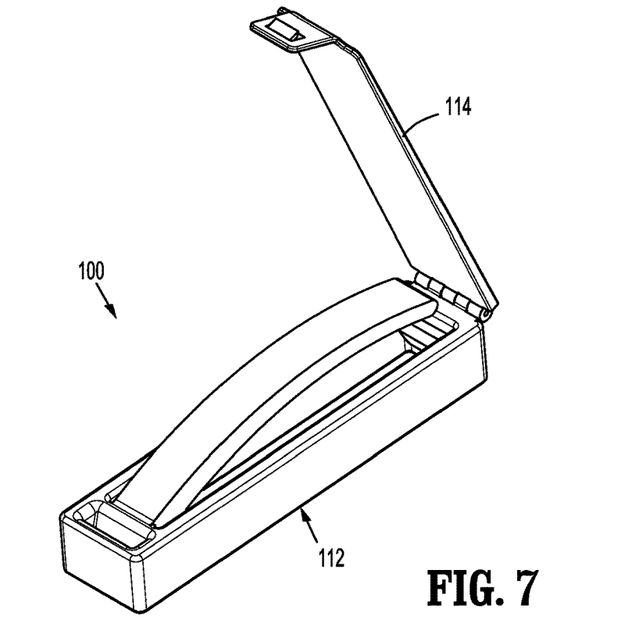
FIG. 7 is a side perspective view of a ligation clip in an open position including other aspects of the disclosure.
Figure 8:
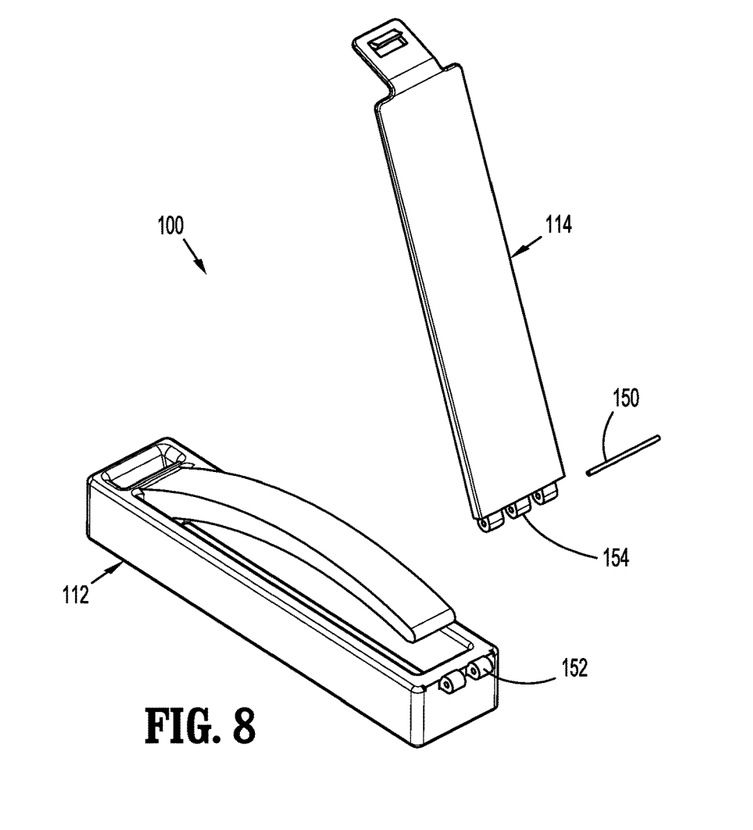
FIG. 8 is a side perspective view of the ligation clip shown in FIG. 7 with a flexible band of the ligation clip separated from a frame of the ligation clip

The flexible band 14 includes a first end portion 36 that is coupled to the first end wall 22 of the frame 12 and a second end portion 38 that supports a latch 40. In aspects of the disclosure, the flexible band 14 is coupled to the frame 12 with a living hinge 42 (FIG. 2). It is envisioned that other coupling devices can be used to secure the flexible band 14 to the frame 12 to facilitate pivoting movement of the flexible beam 14 in relation to the frame 12 between open and clamped positions. For example, in an alternative ligation clip shown generally in FIGS. 7 and 8 as ligation clip 100, the flexible band 114 is pivotably coupled to the frame 112 using a pivot pin 150. In ligation clip 100, the first end portion of the frame 112 includes a first hinge portion 152 and the first end portion of the flexible band 114 includes a second hinge portion 154 that is coupled to the first hinge portion 152 by the pivot pin 150 to facilitate pivotable movement of the flexible band 114 in relation to the frame 112 between the open and clamped positions. The ligation clip 100 also includes a spring beam 116 that is substantially similar to spring beam 16.

Figure 9A:
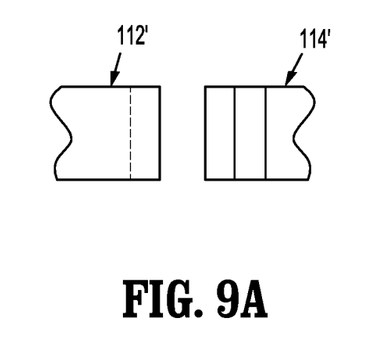
FIG. 9A is a side, cutaway view of an alternative frame and flexible band of the ligation clip shown in FIG. 1 with the parts separated.
Figure 9B:
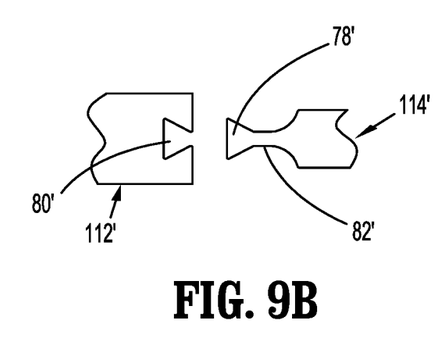
FIG. 9B is a top, cutaway view of the frame and flexible band shown in FIG. 9A.
Figure 10:
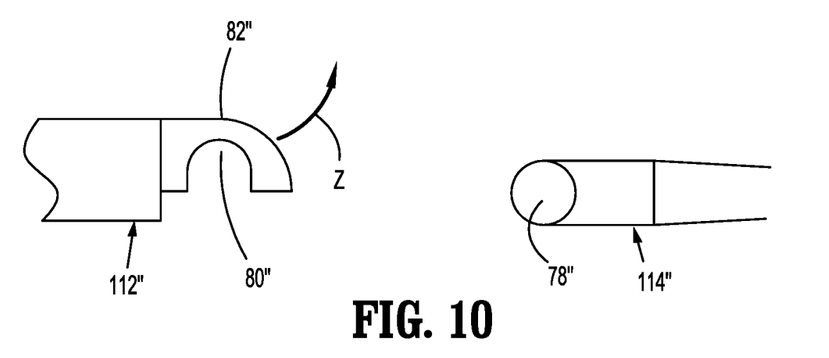
FIG. 10 is a side, cutaway view of another alternative frame and flexible band of the ligation clip shown in FIG. 1 with the parts separated.

It is envisioned that other structure may be used to couple the flexible band 114 to the frame 112. For example, the flexible band 114 and the frame 112 may be connected together using a snap-fit type connection (FIG. 10) or a dove-tail type coupling (FIGS. 9A and 9B). In aspects of the disclosure illustrated in FIGS. 9A and 9B, a first end portion of the flexible band 114' has a dove-tail 78' that is received within a dove-tail slot 80' formed in the first end wall of the frame 112'. The dove-tail 78' defines an area of reduced thickness 82' to facilitate pivotal movement of the flexible band 114' in relation to the frame 112'. In other aspects of the disclosure, the first end portion of the flexible band 114" includes a pivot member 78" that is received within a cylindrical opening 80" defined by a flexible finger 82". The finger 82" is resilient and can flex outwardly in the direction of arrow "Z" to allow the pivot member 78" to be received within the cylindrical opening 80" in snap-fit fashion.

In aspects of the disclosure, the latch 40 includes a flexible tab 44 that is received within the latch slot 30 when the flexible band 14 is moved to the clamped position to secure the flexible band 14 in the clamped position. The flexible tab 44 includes a resilient detent 46 that engages the shoulder 32 (FIG. 3) defined within the latch slot 30 to retain the flexible band 14 in the clamped position. The resilient detent 46 extends outwardly of the flexible tab 44 a distance greater than the width of the latch slot 30 but is deformable inwardly towards the flexible tab 44 to facilitate passage of the detent 46 through the latch slot 30. It is envisioned that other latch structures on the frame 12 and/or the flexible band 14 could be incorporated into the ligation clip 10.

The ligation clip 10 may be formed at least in part of a resilient bioabsorbable and/or biocompatible polymeric material. Examples of suitable bioabsorbable and/or biocompatible polymeric materials include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The ligation clip 10 may also be made at least in part of a polymeric material or materials in combination with radiolucent metal alloys. Alternately, other materials may be used to form the ligation clip 10 including biocompatible metals, plastics and composites.

It is envisioned that the ligation clip 10 can be formed by any known molding process, e.g., injection molding, overmolding or the like. It is also envisioned that the frame 12, the flexible band 14, and the spring beam 16 can be molded as single piece construction.

Figure 5:
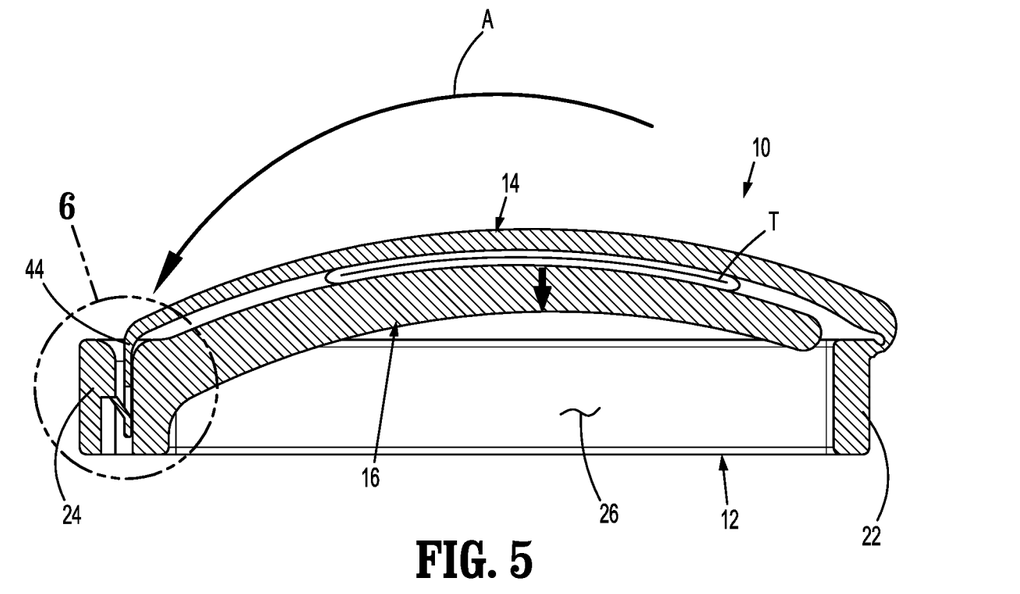
FIG. 5 is a cross-sectional view of the ligation clip shown in FIG. 1 in a clamped position.
Figure 6:
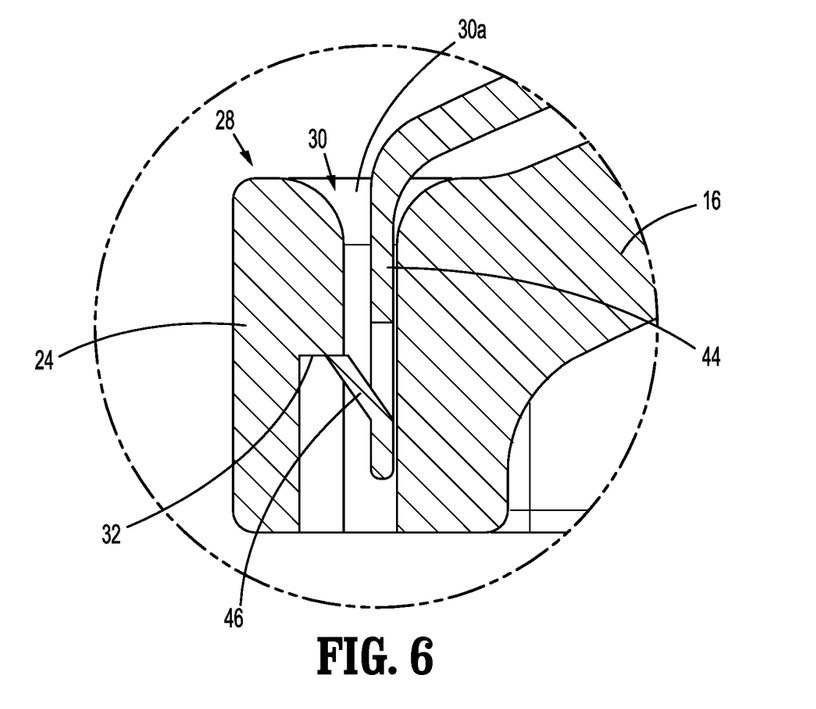
FIG. 6 is an enlarged view of the indicated area of detail shown in FIG. 5.

FIGS. 5 and 6 illustrate the ligation clip 10 in the clamped position. In use of the ligation clip 10, the ligation clip 10 is positioned about tissue "T" in its open position to place the tissue "T" between the flexible band 14 and the spring beam 16. When the tissue "T" is properly positioned within the ligation clip 10, the flexible band 14 is pivoted in the direction of arrow "A" in FIG. 5 to clamp the tissue "T" between the flexible band 14 and the spring beam 16. When the flexible band 14 nears the clamped position, the flexible tab 44 of the latch 40 on the second end portion of the flexible band 14 is inserted into the latch slot 30 of the latch receiver 28 in the frame 12. The inwardly tapered walls 30*a* that define the inlet 30*a* to the latch slot 30 guide the flexible tab 44 into the latch slot 30. As the flexible tab 44 is advanced through the latch slot 30, the detent 46 of the latch 28 is deformed inwardly and passes through the latch slot 30 until the resilient detent 46 passes the shoulder 32. When the resilient detent 46 passes the shoulder 32 within the latch slot 30, the resilient detent 46 snaps outwardly into engagement with the shoulder 32 to retain the flexible band 14 in the position.

Persons skilled in the art will understand that the devices and methods specifically described herein and illustrated in the accompanying drawings are non-limiting exemplary aspects of the disclosed ligation clip. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosed ligation clip. Accordingly, the disclosure is not to be limited by what has been particularly shown and described, except as indicated by the appended claims.

What is claimed is:

1. A ligation clip comprising:
   a frame having a first end portion, a second end portion, and spaced side walls, the frame defining a cavity between the side walls, the second end portion of the frame defining a latch receiver;
   a flexible band having a first end portion coupled to the first end portion of the frame and a second end portion supporting a latch, the flexible band being moveable in relation to the frame from an open position to a clamped position, the latch received within the latch receiver in the clamped position to retain the flexible band in the clamped position; and
   a spring beam secured to the second end portion of the frame in cantilevered fashion, the spring beam extending over the cavity defined by the frame.

2. The ligation clip of claim 1, wherein the frame has a rectangular configuration.

3. The ligation clip of claim 2, wherein the flexible band is coupled to the first end portion of the frame by a living hinge.

4. The ligation clip of claim 2, wherein the first end portion of the frame includes a first hinge portion and the first end portion of the flexible band includes second hinge portion, the first hinge portion coupled to the second hinge portion by a pivot pin.

5. The ligation clip of claim 2, wherein the first end portion of the frame is coupled to the first end portion of the flexible band by a dove-tail type connection.

6. The ligation clip of claim 2, wherein the latch receiver includes a latch slot that receives the latch to retain the flexible beam in the clamped position.

7. The ligation clip of claim 6, wherein the latch slot defines a shoulder.

8. The ligation clip of claim 7, wherein the latch includes a flexible tab that is received within the latch slot when the flexible beam is in the clamped position.

9. The ligation clip of claim 8, wherein the flexible tab of the latch supports a detent, the detent engaging the shoulder defined within the latch slot when the flexible beam is in the clamped position to retain the flexible beam in the clamped position.

10. The ligation clip of claim 6, wherein the latch slot includes an inlet opening that defines an inwardly tapered guide surface.

11. The ligation clip of claim 1, wherein the ligation clip is formed as a single piece using a molding process.

12. The ligation clip of claim 1, wherein the spring beam includes a curved body formed of a resilient material, the curved body including a central portion that bows upwardly away from the cavity of the frame.

13. A ligation clip comprising:
    a frame having a first end portion, a second end portion, and spaced side walls, the frame having a rectangular configuration and defining a cavity between the side walls, the second end portion of the frame defining a latch receiver;
    a flexible band having a first end portion coupled to the first end portion of the frame and a second end portion supporting a latch, the flexible band being moveable in relation to the frame from an open position to a clamped position, the latch received within the latch receiver in the clamped position to retain the flexible band in the clamped position; and
    a spring beam secured in cantilevered fashion to the second end portion of the frame, the spring beam being positioned over the cavity defined by the frame and having a curved body including a central portion that bows upwardly away from the cavity of the frame.

14. The ligation clip of claim 13, wherein the flexible band is coupled to the first end portion of the frame by a living hinge.

15. The ligation clip of claim 13, further including a pivot pin, wherein the first end portion of the frame includes a first hinge portion and the first end portion of the flexible band includes second hinge portion, the first hinge portion coupled to the second hinge portion by the pivot pin.

16. The ligation clip of claim 13, wherein the latch receiver includes a latch slot that defines a shoulder and the latch includes a flexible tab that is received within the latch slot when the flexible beam is in the clamped position.

17. The ligation clip of claim 16, wherein the flexible tab of the latch supports a detent, the detent engaging the shoulder defined within the latch slot when the flexible beam is in the clamped position to retain the flexible beam in the clamped position.

18. A ligation clip comprising:
- a frame having a first end portion, a second end portion, and spaced side walls, the frame having a rectangular configuration and defining a cavity between the side walls, the second end portion of the frame defining a latch receiver, the latch receiver including a latch slot that defines a shoulder;
- a flexible band having a first end portion coupled to the first end portion of the frame and a second end portion supporting a latch, the flexible band being moveable in relation to the frame from an open position to a clamped position, the latch including a flexible tab that is received within the latch slot of the latch receiver, the flexible tab of the latch supporting a detent that engages the shoulder defined within the latch slot when the flexible beam is in the clamped position to retain the flexible beam in the clamped position; and
- a spring beam secured in cantilevered fashion to the second end portion of the frame, the spring beam being positioned over the cavity defined by the frame.

19. The ligation clip of claim 18, wherein the flexible band is coupled to the first end portion of the frame by a living hinge.

20. The ligation clip of claim 18, further including a pivot pin, wherein the first end portion of the frame includes a first hinge portion and the first end portion of the flexible band includes second hinge portion, the first hinge portion coupled to the second hinge portion by the pivot pin.

\* \* \* \* \*